(12) United States Patent
Daly et al.

(10) Patent No.: US 6,465,623 B2
(45) Date of Patent: *Oct. 15, 2002

(54) GDU, A NOVEL SIGNALLING PROTEIN

(75) Inventors: Roger John Daly, Alexandria; Robert Lindsay Sutherland, Lindfield, both of (AU)

(73) Assignee: Garvan Institute of Medical Research, Darlinghurst (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,771
(22) PCT Filed: May 2, 1996
(86) PCT No.: PCT/US96/00258
§ 371 (c)(1), (2), (4) Date: Apr. 22, 1998
(87) PCT Pub. No.: WO96/34951
PCT Pub. Date: Nov. 7, 1996

(65) Prior Publication Data
US 2002/0086328 A1 Jul. 4, 2002

(30) Foreign Application Priority Data
May 2, 1995 (AU) .............................. PN 2742

(51) Int. Cl.⁷ ...................... C07K 16/00; G01N 33/53; G01N 33/574
(52) U.S. Cl. ...................... 530/388.1; 435/7.1; 435/7.2; 435/7.23
(58) Field of Search ................ 435/7.1, 7.2, 7.21, 435/7.23; 530/387.1, 388.1

(56) References Cited

U.S. PATENT DOCUMENTS
5,677,421 A * 10/1997 Schlessinger et al.

FOREIGN PATENT DOCUMENTS

| | | |
|---|---|---|
| AU | 25185/92 | 4/1993 |
| AU | 53633/94 | 5/1994 |
| AU | 51804/93 | 6/1994 |
| AU | 19809/95 | 9/1995 |
| AU | 21022/95 | 9/1995 |
| EP | 400976 | 1/1994 |
| EP | 412707 | 2/1994 |
| EP | 426520 | 6/1994 |
| EP | 370764 | 1/1995 |
| EP | 240350 | 6/1995 |
| WO | WO 90/08160 | 7/1990 |
| WO | WO 90/14357 | 11/1990 |
| WO | WO 92/10161 | 6/1992 |
| WO | WO 93/05148 | 3/1993 |
| WO | WO 93/19074 | 9/1993 |
| WO | WO 94/08557 | 4/1994 |
| WO | WO 95/24205 | 9/1995 |
| WO | WO 95/24426 | 9/1995 |

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Alberts et al. (Molecular Biology of the Cell, 3rd edition, 1994, p. 465).*
Shantz and Pegg (Int J of Biochem and Cell Biol., 1999, vol. 31, pp. 107–122).*
McClean and Hill (Eur J of Cancer, 1993, vol. 29A, pp. 2243–2248).*
Fu et al (EMBO Journal, 1996, vol. 15, pp. 4392–4401).*
Burgess et al. (J. of Cell Bio. 111:2129–2138, 1990).*
Bowie et al. (Science, 1990, 257:1306–1310).*
Lazar et al. (Molecular and Cellular Biology, 1988, 8:1247–1252).*
Bork (Genome Research, 2000, 10:398–400).*
Schlessinger et al., Issued Patents Database, US Patent & Trademark Office, protein–protein matching, Arlington, VA 22202, 1994.*
Cohen et al., "Modular binding domains in signal transduction proteins" *Cell* (1995) 80:237–248.
Daly, "SH2 domain–containing signaling proteins in human breast cancer" *Breast Cancer Res. Treat.* (1995) 34:85–92.
Fazioli et al., "Eps8, a substrate for the epidermal growth factor receptor kinase, enhances EGF–dependant mitogenic signals" *EMBO J.*(1993) 12(10):3799–3808.
Heidaran et al., "Deletion or substitution within the α platelet–derived growth factor receptor kinase insert domain: Effects on fucntional coupling with intracellular signaling pathways" *Mol. Cell. Biol.* (1991) 11(1): 134–142.
Honegger et al., "A mutant epidermal growth factor receptor with defective protein tyrosine kinase is unable to stimulate proto–oncogene expression and DNA synthesis" *Mol. Cell. Biol.* (1987)7(12):4568–4571.
Kashles et al., "A dominant negative mutation suppresses the function of normal epidermal growth factor receptors by heterodimerization" *Mol. Cell. Biol.* (1991) 11(3):1454–1463.
Koch et al., "SH2 and SH3 domains: Elements that control interactions of cytoplasmic signaling proteins" *Science* (1991) 252(3):668–674.
Liu et al., "Grb–IR: A SH2 domain containing protein that binds to the insulin receptor and inhibits its function" *Proc. Natl. Acad. Sci. USA* (1995)92(22):10287–10291.

(List continued on next page.)

Primary Examiner—Susan Ungar
Assistant Examiner—Gary B. Nickol
(74) Attorney, Agent, or Firm—Morrison & Foerster LLP (57) ABSTRACT

The present invention provides the nucleotide and amino acid sequence of a previously unidentified erbB receptor target.

2 Claims, 3 Drawing Sheets

OTHER PUBLICATIONS

Lowenstein et al., "The SH2 and SH3 domain–containing protein GRB2 links recpetor tyrosine kinases to ras signaling" *Cell* (1992) 70:431–442.

Margolis et al., "High–efficiency expression/cloning of epidermal growth factor–receptor–binding proteins with Src homology 2 domains" *Proc. Natl. Acad. Sci. USA* (1992)89(19):8894–8898.

Ooi et al., "The cloning of Grb 10 reveals a new family of SH2 domain proteins" *Oncogene* (1995) 10(8):1621–1630.

Osherov et al., "Selective inhibition of the epidermal growth factor and HER2/Neu receptors by tyrphostins" *J. Biol. Chem.* (1993) 268(15):11134–11142.

Redemann et al., "Anti–oncogenic activity of signalling–defective epidermal growth factor receptor mutants" *Mol. Cell. Biol.* (1992) 12(2):491–498.

Schlessinger et al., "Growth factor signaling by receptor tyrosine kinases" *Neuron* (1992) 9:383–391.

Shepard et al., "Monoclonal antibody therapy of human cancer: Taking the HER 2 protooncogene to the clinic" *J. Clin. Immunol.* (1991) 11(3):117–127.

Skolnik et al., "Cloning of P13 kinase–associated p85 utilizing a novel method for expression/cloning of target proteins for receptor tyrosine kinases" *Cell* (1991) 65:83–90.

Slamon et al., "Studies of the HER–2/neu proto–oncogene in human breast and ovarian cancer" *Science* (1989) 244(12):707–712.

Stein et al., "The SH2 domain GRB–7 is co–amplified, overexpressed and in a tight complex with HER2 in breast cancer" *EMBO J.* (1994) 13(6):1331–1340.

Trahey et al., "Molecular cloning of two types of GAP complementary DNA from human placenta" *Science* (1988) 242:1696–1700.

von Rüden et al., "Expression of functional human EGF receptor on murine bone marrow cells" *EMBO J.* (1988) 7(9):2749–2756..

White et al., "Characterization of an endogenous substrate of the insulin receptor in cultured cells" *J. Biol. Chem.* (1987) 262(20):9769–9777.

* cited by examiner

```
CGGATGAGGGTCAGGGCTGCGCGGACCCCTATCCCGCCTGCGTCCTCCCGGCAAGCCCAGCGGGAGCGCC    70
CGCTCGGCTGGGTCCCCGCCTCCAGCGCGCCGGGGCCGCCCAGACCCTGGGCTCAGCCTCGCGCCCCGGT   140
GCCCACCTGAGGAGGCGGCGGTCCCGGCCTCGCGTCCCGGATGGGACGGCGCGGGAGCAATGCCAGTGGC   210
CCCGAGCGCCCCGGGCCACGCGCGGGGCCGGCCAGCCGCTCTCGCGCCCTCCCCGCCCCCTCCGCGCCTT   280
GCCTCGCCGCCCGCGCGCCCCACCCACCGGCCGCTCCTCCCCTCTCCCCACCCTCCTCCTCCGCCCCCTC   350
CCCTCCCCCGCCGCCTCGCAGATAGCTCGGCCGCGCGTCTCAGCCGCCGGGGCCCCGAGCGCAGGCGGCG   420
AGGCCACCACACCTGCAGAGCGCTCGGGCTGCCTAGGCGGCACCTCGCCTCCCGCCGCGCAAACCCCTTC   490
TCCCCACGCGCCGAGTCTCCCATGACGCCCGAGCCCCCCGGCCGGCGACAATGACCACTTCCCTGCAAGA   560
                                                         M  T  T  S  L  Q  D
TGGGCAGAGCGCCGCGAGCAGGGCGGCTGCCCGGGATTCGCCGCTGGCCGCCCAGGTGTGTGGCGCTGCC   630
 G  Q  S  A  A  S  R  A  A  A  R  D  S  P  L  A  A  Q  V  C  G  A  A
CAGGGGAGGGGCGACGCCCACGACCTGGCGCCGGCCCCCTGGCTGCACGCGCGAGCGCTCCTGCCCCTTC   700
 Q  G  R  G  D  A  H  D  L  A  P  A  P  W  L  H  A  R  A  L  L  P  L
CGGACGGGACCCGCGGCTGTGCTGCAGACAGGAGAAAAAGAAAGATCTTGATGTTCCGGAAATGCCATC   770
 P  D  G  T  R  G  C  A  A  D  R  R  K  K  K  D  L  D  V  P  E  M  P  S
TATTCCAAACCCTTTTCCTGAGCTATGCTGTTCTCCAATTACATCTGTGTTGTCAGCAGACCTATTTCCC   840
 I  P  N  P  F  P  E  L  C  C  S  P  I  T  S  V  L  S  A  D  L  F  P
AAAGCAAATTCAAGGAAAAAACAGGTGATTAAAGTATACAGTGAAGATGAAACCAGCAGGGCTTTAGATG   910
 K  A  N  S  R  K  K  Q  V  I  K  V  Y  S  E  D  E  T  S  R  A  L  D
TACCCAGTGACATAACGGCTCGAGATGTTTGTCAGCTGTTGATCCTGAAGAATCATTACATTGATGACCA   980
 V  P  S  D  I  T  A  R  D  V  C  Q  L  L  I  L  K  N  H  Y  I  D  D  H
CAGCTGGACCCTTTTTGAGCACCTGCCTCACATAGGTGTAGAAAGAACAATAGAAGACCACGAACTGGTG  1050
 S  W  T  L  F  E  H  L  P  H  I  G  V  E  R  T  I  E  D  H  E  L  V
ATTGAAGTGCTATCCAACTGGGGGATAGAAGAAGAAACAAACTATACTTTAGAAAAAATTATGCCAAAT  1120
 I  E  V  L  S  N  W  G  I  E  E  E  N  K  L  Y  F  R  K  N  Y  A  K
ATGAGTTCTTTAAAAACCCAATGTATTTTTTTCCAGAGCATATGGTATCTTTTGCAACTGAAACCAATGG  1190
 Y  E  F  F  K  N  P  M  Y  F  F  P  E  H  M  V  S  F  A  T  E  T  N  G
TGAAATATCCCCCACACAGATTTTGCAGATGTTTCTGAGTTCAAGCACATATCCTGAAATTCATGGTTTC  1260
 E  I  S  P  T  Q  I  L  Q  M  F  L  S  S  S  T  Y  <u>P  E  I  H  G  F</u>
TTACATGCGAAAGAACAGGGAAAGAAGTCTTGGAAAAAAATTTACTTTTTTCTAAGAAGATCTGGTTTAT  1330
<u>L  H  A  K  E  Q  G  K  K  K  S  W  K  K  I  Y  F  F  L  R  R  S  G  L</u>
ATTTTTCTACTAAAGGAACATCAAAGGAACCGCGGCATTTGCAGTTTTTCAGCGAATTTGGCAATAGTGA  1400
<u>Y  F  S  T  K  G  T  S  K  E  P  R  H  L  Q  F  F  S  E  F  G  N  S  D</u>
TATTTATGTGTCACTGGCAGGCAAAAAAAAAACATGGAGCACCGACTAACTATGGATTCTGCTTTAAGCCT  1470
<u>I  Y  V  S  L  A  G  K  K  K  H  G  A  P  T  N  Y  G  F  C  F  K  P</u>
AACAAAGCGGGAGGGCCCCGAGACCTGAAAATGCTCTGTGCAGAAGAAGAGCAGAGTAGGACGTGCTGGG  1540
<u>N  K  A  G  G  P  R  D  L  K  M  L  C  A  E  E  E  Q  S  R  T  C  W</u>
TGACCGCGATTAGATTGCTTAAGTATGGCATGCAGCTGTACCAGAATTATATGCATCCATATCAAGGTAG  1610
<u>V  T  A  I  R  L  L</u>  K  Y  G  M  Q  L  Y  Q  N  Y  M  H  P  Y  Q  G  R
AAGTGGCTGCAGTTCACAGAGCATATCACCTATGAGAAGTATATCAGAGAATTCCCTGGTAGCAATGGAC  1680
 S  G  C  S  S  Q  S  I  S  P  M  R  S  I  S  E  N  S  L  V  A  M  D
TTCTCAGGCCAGAAAAGCAGAGTTATAGAAAATCCCACTGAAGCCCTTTCAGTTGCGGTTGAAGAAGGAC  1750
 F  S  G  Q  K  S  R  V  I  E  N  P  T  E  A  L  S  V  A  V  E  E  G
TCGCTTGGAGGAAAAAAGGATGTTTACGCCTGGGCACTCACGGTAGCCCCACTGCCTCTTCACAGAGCTC  1820
 L  A  W  R  K  K  G  C  L  R  L  G  T  H  G  S  P  T  A  S  S  Q  S  S
TGCCACAAACATGGCTATCCACCGGTCCCAGCCATGGTTTCACCACAAAATTTCTAGAGATGAGGCTCAG  1890
 A  T  N  M  A  I  H  R  S  Q  P  W  F  H  H  K  I  S  R  D  E  A  Q
CGATTGATTATTCAGCAAGGACTTGTGGATGGAGTTTTCTTGGTACGGGATAGTCAGAGTAACCCCAAAA  1960
 R  L  I  I  Q  Q  G  L  V  D  G  V  F  L  V  R  D  S  Q  S  N  P  K
CTTTCGTACTGTCAATGAGTCATGGACAAAAAATAAAGCACTTTCAAATTATACCAGTAGAAGATGACGG  2030
 T  F  V  L  S  M  S  H  G  Q  K  I  K  H  F  Q  I  I  P  V  E  D  D  G
TGAAATGTTCCACACACTGGATGATGGCCACACAAGATTTACAGATCTAATACAGCTGGTGGAGTTCTAT  2100
 E  M  F  H  T  L  D  D  G  H  T  R  F  T  D  L  I  Q  L  V  E  F  Y
CAACTCAATAAGGGCGTTCTTCCTTGCAAGTTGAAACATTATTGTGCTAGGATTGCTCTCTAGACAAGCC  2170
 Q  L  N  K  G  V  L  P  C  K  L  K  H  Y  C  A  R  I  A  L  *
AGAAGTGACTTATTAAACTATTGAAGGAAAAGGACTCAAGAAAAATAATAAAAGACCATAAATAAGGGCG  2240
AAAACATTATCATGTGAAAAGAATGTATTTCACCTGCAAGTTACAAAAAAATAGTTTGTGCATTGCAAAT  2310
AAGCAAAGACTTGGATTGACTTTACATTCATCATTTAAAATTCATTAGTTAAAATTAAACCTTAGGAAAA  2380
AAAAAAAAAAAAAAAAAAAAAAAA                                                2404
```

```
Grb14     1   MTTSLQDGQSAASRAAARDSPLAAQVCGAAQGRGDAHDLAPAPWLHA          47
Grb7      1   MELDLSPTHLSSSPE---------DVCPTPATPPETPPPPDNP----         34
Grb10     1   MNNDINSSVESLNSACNMQSDTDTAPLLEDGQHASNQGAASSSRGQP         47

Grb14    48   RALLPLPDGTRGCAAD--RR---KKKDLDVPEMPSIPNPFPEL----         85
Grb7     35   ----PPGDVKRSQLPIPSSRKLREEEFQATSLPSIPNPFPELCS--         75
Grb10    48   QAS-PRQKMQRSQPVHILRRLQEEDQQLRTASLPAIPNPFPELTGAA         93

Grb14    86   ------------------------C---CS-----------------         88
Grb7     76   --------------PPSQKP-----------ILGGSSGARG------         91
Grb10    94   PGSPPSVAPSSLPPPPSQPPAKHCGRCEKWIPGENTRGNGKRKIWRW        140

Grb14    89   -------PITSVLSADLFPKANSR--KKQV-----------------        109
Grb7     92   --------------LLPRDSSRL---------CV-------------        102
Grb10   141   QFPPGFQLSKLTRPGLWTKTTARFSKKQPKNQCPTDTVNPVARMPTS        187

Grb14   110   ----------KVYSEDETSRALDVPSDITARDVCQLLILKNHYIDD        146
Grb7    103   ----------VKVYSEDGACRSVEVAAGATARHVCEMLVQRAHALSD        139
Grb10   188   QMEKLRLRKDVKVFSEDGTSKVVEILTDMTARDLCQLLVYKSHCVDD        234
F10E9.6 187                VKFFVEDGEALQLLIDERWTVADTLKQLAEKNHIALM        232

Grb14   147   HSWTLEEHLPHIGVERTIEDHELVIEVLSNWGIEEENKLYFRKNYAK        193
Grb7    140   ESWGLVESHPYLALERGLEDHEFVVEVQEAWPVGGDSRFIFRKNFAK        186
Grb10   235   NSWTLVEHHHPQLGLERCLEDHEIVVQVEST--MPSESKFLFRKNYAK        279
F10E9.6 233   EDHCIVEEYPELYIKRVYEDHEKVVENIQMWVQDSPNKLYFMRRPDK        279

Grb14   194   YEFFKNPMY-FFPEHMVSFATETNGEISPTQILQMFLS------SST        233
Grb7    187   YELFKSPPHTLFPEKMVSSCLDAQTGISHEDLIQNFLN------AGS        227
Grb10   280   YEFFKNPVN-FLPDQMVNWCQQSNG--GQAQLLQNFLN------TSS        317
F10E9.6 280   YALFISRPELYLLTPKTSDHMEIPSGDQWTIDVKQKFVSEYFHREPVV        326

Grb14   234   YPEIHGFLHAKEQGK----KSWKKIYFFLRRSGLYFSTKGTSKEPRH        276
Grb7    228   FPEIQGFLQLRGSGRGSGRKLWKRFFCFLRRSGLYYSTKGTSKDPRH        274
Grb10   318   CPEIQGFLQVKEVGR----KSWKKLYVCLRRSGLYYSTKGTSKEPRH        360
F10E9.6 327   PPEMEGFLYLKSDGR----KSWKKHYFVLRPSGLYYAPKSKKPTTKD        369

Grb14   277   LQFFSEFGNSDIYVSLAGKKHGAPTNYGFCFKPNKA-GGPRDL-KM        321
Grb7    275   LQYVADVNESNVYVVTQGRKLYGMPTDFGFCVKPNKLRNGHKGL-HI        320
Grb10   361   LQLLADLEESSIFYLIAGKKQYNAPNEHGMCIKPNKAKTEMKELL-RL        406
F10E9.6 370   LTCLMNLHSNQVYTGIGWEKKYKSPTPWCISIKLTALQMKRSQFIKY        416

Grb14   322   LCAELEQSRTCWVTAIRLLKYGMQLYQNYMHPYQGRSGC--SSQSIS        366
Grb7    321   FCSEDEQSRTCWLAAFRLFKYGVQLYKNYQQAQSRHLRL--SYLGSP        365
Grb10   407   LCAEDEQIRTCWMTAFRLLKYGMLLYQNYRIP--QRKGL--PPPFNA        449
F10E9.6 417   ICAEDEMTFKKWLVALRIAKNGAELLENYERACQIRRETLGPASSMS        463

Grb14   367   PMRSISENSLVAMDFSGQK------------SRVIENPTEALSVAVE        401
Grb7    366   PLRSVSDNTLVAMDFSGHA------------GRVIDNPREALSAAME        400
Grb10   450   PMRSVSENSLVAMDFSGQI------------GRVIDNPAEAQSAALE        484
F10E9.6 464   AASSSTAISELVPHSLSHHQRTPSVASSIQLSSHMMNNPTHPLSVNV-        509

Grb14   402   EGLAWRKKGCLRLGTHGSPTASSQSSATNMAIHRSQPWFHHKISRDE        448
Grb7    401   EAQAWRKKTNHRLSL----PTTCSGSSLSAAIHRTQPWFHGRISREE        443
Grb10   485   EGHAWRN-GSTRMNILSSQSPL-HPSTLNAVIHRTQHWFHGRISREE        529
F10E9.6 510   -----RNQSPASFSVNSCQQ--SHPSRTSAKL                        534

Grb14   449   AQRLIIQQGLVDGVFLVRDSQSNPKTFVLSMSHGQKIKHFQIIPVED        495
Grb7    444   SQRLIGQQGLVDGVFLVRESQRNPQGFVLSLCHLQKVKHYLILPSED        490
Grb10   530   SHRIIKQQGLVDGLFLLRDSQSNPKAFVLTLCHHQKIKNFQILPCED        576

Grb14   496   DGEMFHTLDDGHTRFTDLIQLVEFYQLNKGVLPCKLKHYCARIAL          540
Grb7    491   EGCLYFSMDEGQTRFTDLLQLVEFHQLNRGILPCLLRHCCARVAL          535
Grb10   577   DGQTFFTLDDGNTKFSDLIQLVDFYQLNKGVLPCKLKHHCIRVAL          621
```

FIGURE 3

GDU, A NOVEL SIGNALLING PROTEIN

CROSS-REFERENCE TO RELATED APPLICATIONS

This application is based on PCT Application No. PCT/AU96/00258, filed May 2, 1996; which is a continuation of Australian Patent Application No. PN 2742, filed May 2, 1995.

The present invention relates to a previously unidentified erbB receptor target designated GDU. The present invention relates to a polynucleotide encoding GDU and to methods of detecting the presence of GDU.

Many intracellular targets for receptor tyrosine kinases (RTKs) contain one or more src homology (SH)2 domains. These are conserved, non-catalytic domains of approximately 100 amino acids which bind to short peptide sequences containing phosphotyrosine (Cohen et al, Cell 80, 237–248, 1995). Since receptor autophosphorylation on specific tyrosine residues follows RTK activation, SH2 domains mediate receptor-substrate, as well as other protein-protein interactions, during signal transduction. SH2 domains contain not only a pocket lined with basic residues which binds the phosphotyrosine but also an additional binding pocket or groove which interacts with amino acids C-terminal to this residue, this determining the specificity of the interaction. The particular autophosphorylation sites present on a given RTK therefore define the SH2 domain-containing signalling proteins that it can recruit and hence, to a large extent, the signalling specificity of the receptor. SH2 domains are often accompanied in signalling proteins by two other conserved protein modules; SH3 domains, which bind to proline-rich peptide ligands, and pleckstrin-homology (PH) domains. The function of the latter remains ill-defined, and both protein and phospholipid ligands have been described.

SH2 domain-containing proteins can be divided into two classes (Schlessinger and Ullrich Neuron, 9,383–301 1992); Class I, which also possess a catalytic function e.g. phospholipase C-γ1 (PLC-γ1) and the GTPase activating protein for Ras (Ras-GAP), and Class II, which contain only non-catalytic protein modules and are thought to function as adaptors, linking separate catalytic subunits to receptors or other signalling proteins e.g. Grb2. The tissue expression of particular SH2 domain-containing proteins varies from ubiquitous, e.g. Grb2, which performs a fundamental role in linking tyrosine kinases to Ras signalling, to relatively restricted e.g. Grb7, which is mainly expressed in the liver and kidney (Margolis et al Proc. Natl. Acad. Sci. USA, 89, 8894–8898, 1992). Presumably the latter protein performs relatively specialised signalling functions. The CORT (cloning of receptor targets) technique, in which cDNA expressionlibranes are screened with the tyrosine phosphorylated C-terminus of the EGF receptor represents a powerful methodology for the identification and characterisation of novel, SH2 domain-containing, receptor substrates (Skolnik et al Cell 65, 83–90, 1991).

Members of the erbB family of RTKs and their ligands are implicated both in normal mammary gland development and the growth and progression of human breast cancer. Furthermore, marked alterations in the expression or activity of several SH2 domain-containing proteins have been observed in human breast cancers or breast cancer-derived cell lines, suggesting that this represents an additional level at which RTK signalling may be modulated in this disease (Daly, Breast Cancer Res Treat, 34, 85–92, 1995). We therefore chose normal human mammary epithelial cells as a basis for a CORT screening program and hence identification of novel, and relatively tissue specific, erbB receptor targets.

Screening of a HMEC 184 λEXlox cDNA library isolated 1 Ras-GAP, 2 Grb2 cDNAs and a cDNA encoding a novel SH2 domain-containing protein. This protein, designated GDU or Grb14 (the designations "GDU" and "Grb14" are used interchangeably herein), is related both in molecular architecture and sequence homology to Grb7 and Grb10, previously identified erbB receptor targets. These three proteins also share significant sequence homology, over an approximately 300 amino acid region encompassing the PH domain, with the C. elegans gene F10E9.6. The latter gene has recently been shown to encode a protein (mig. 10) critical for longitudinal neuronal migration in C. elegans; members of the Grb7 gene family, including GDU, may therefore be involved in the regulation of cell migration in higher organisms.

Analysis of GDU gene expression in normal breast epithelial cells and a large series of human breast cancer cell lines revealed that expression was limited predominantly to normal breast cells and the more highly differentiated, estrogen receptor positive, breast cancer cell lines. Also, GDU mRNA was overexpressed in the DU-145 prostate carcinoma cell line relative to the normal prostate and two other prostate cancer cell lines. GDU may therefore serve as a prognostic indicator and/or a tumour marker in both breast and prostate cancer. Furthermore, since altered expression of GDU may contribute to the abnormal proliferation, invasion and/or migration of cancer cells, GDU signal transduction may provide a novel therapeutic target in human cancer. Finally, since GDU is involved in downstream signalling initiated by the platelet derived growth factor receptor (PDGFR), it may provide a target in diseases or conditions in which PDGF plays a regulatory role e.g. wound healing, fibrotic conditions, atherosclerosis.

In a first aspect the present invention consists in a polynucleotide encoding GDU, the polynucleotide having a sequence which encodes a polypeptide having an amino acid sequence as shown in FIG. 2 or a sequence which hybridises thereto.

In a preferred embodiment of the present invention the polynucleotide has a sequence as shown in FIG. 2.

In a second aspect the present invention consists in a polypeptide, the polypeptide having an amino acid sequence as shown in FIG. 2.

In a third aspect the present invention consists in an antibody which binds to the polypeptide of the second aspect of the present invention.

The antibody may be monoclonal or polyclonal, however, it is presently preferred that the antibody is a monoclonal antibody.

In a fourth aspect, the present invention consists in an oligonucleotide probe of at least 12 nucleotides, the oligonucleotide probe having a sequence such that the probe selectively hybridises to the polynucleotide of the first aspect of the present invention under stringent conditions.

In a preferred embodiment of this aspect of the present invention the oligonucleotide is labelled. In a further preferred embodiment of the present invention the oligonucleotide is of at least 18 nucleotides.

In a fifth aspect the present invention consists in method of detecting the presence of GDU in a sample, the method comprising reacting the sample with an antibody of the second aspect of the present invention or a oligonucleotide probe of the fourth aspect of the present invention and detecting the binding of the antibody or the probe.

In order that the nature of the present invention may be more clearly understood preferred forms thereof will now be described with reference to the following examples and Figures in which:

FIG. 2 shows the nucleotide and amino acid sequence of Grb14. The PH domain is underlined and the SH2 domain indicated by bold type. The translation termination codon is shown by an asterisk in the amino acid sequence. Numbers refer to distances in bp.

FIG. 3 shows the sequence homology between Grb14, (SEQ ID:2), Grb7, (SEQ ID:3), Grb10 (SEQ ID:4), and F10E9.6. As alignment of the amino acid sequences of Grb14, mouse Grb7, mouse Grb10 and C. elegans F10E9.6 was obtained using the computer programs Clustal W and SeqVu. Identical residues are boxed. A highly conserved proline-rich motif is indicated by the dotted underline, the PH domain by the broken underline and the SH2 domain by the bold underline. Only the central region of F10E9.6 exhibiting homology with the Grb7 family is shown. Amino acid residues for each protein are numbered (from the initiation methionine) on the right.

Screening of a Normal Breast Epithelial Cell cDNA Library by the CORT Technique

CORT screening of two cDNA libraries prepared from normal breast epithelial cells led to the isolation of recombinants which exhibited differential binding to the phosphorylated EGFR C-terminus. Upon excision of the corresponding pEXIox plasmids and sequencing of the DNA inserts, two recombinants which bound very strongly were identified as Grb2 cDNA clones (Lowenstein et al 1992, Cell 70, 431–442, 1992), and a clone exhibiting moderate binding corresponded to ras-GAP (Trahey et al. Science 242, 1696–1700, 1988). The final clone, designated GDU, bound only weakly to the EGFR. A database search with the corresponding cDNA sequence did not detect an exact match but revealed significant sequence homology with the SH2 domain-containing protein Grb7 (Margolis et al PNAS 89, 8894–8898, 1992). The cDNA (GDU Clone 1 in FIG. 1) encoded a short stretch of amino acids followed by a C-terminal SH2 domain; homology to Grb7 was apparent over this entire open reading frame.

Characterisation of GDU

Figure 1:
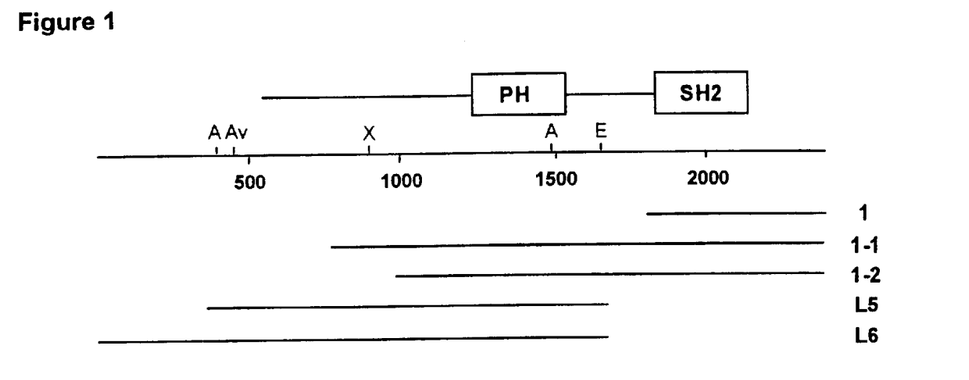
FIG. 1 shows a schematic representation of Grb14 structure with a restriction map for the Grb14 cDNA and the cDNA clones used to derive the Grb14 sequence aligned underneath. The initial clone isolated by CORT screening was designated clone 1. Two other clones (1-1 and 1-2) were isolated from the 184 cell line library by screening using clone 1 as a probe. The Grb14 cDNA sequence was completed using two clones L5 and L6, isolated from a human liver cDNA library. Abbreviations are as follows: A; Apa I; Av; Avr II, X; Xho I; E; Eco RI. The numbers refer to distance in bp.

In order to obtain the full length cDNA sequence for GDU, two cDNA library screens were performed. In the first, the cDNA insert from Clone 1 was used to screen the breast cDNA library. Screening of $5 \times 10^5$ recombinants isolated 2 cDNAs, designated 1-1 and 1-2, of 1.6 and 1.4 kb, respectively (FIG. 1). In the second, a 213bp EcoRI-Xho I restriction fragment derived from 1-1 (FIG. 1) was used to screen a human liver cDNA library. Screening of $1 \times 10^6$ recombinants isolated 2 cDNAs, designated L5 and L6, of 1.3 and 1.7 kb, respectively (FIG. 1). Clones 1-1, 1-2, L5 and L6 were sequenced in their entirety on both strands to obtain the cDNA sequence shown in FIG. 2. The 2.4 kb of DNA sequence derived from these overlapping clones corresponds closely to the size of the three most abundant mRNA species detected upon Northern blot analysis.

Analysis of the cDNA sequence identified an open reading frame of 540 amino acids. The initiation codon is preceded by an in-frame termination codon and is surrounded by a consensus sequence for strong translational initiation. The encoded protein is similar both in molecular architecture and amino acid sequence to Grb7 (Margolis et al, Proc. Natl. Acad. Sci. USA 89, 8894–8898, 1992) and the recently identified Grb10 (Ooi et al, Oncogene 10, 1621–1630, 1995), consisting of a N-terminal region containing at least one proline-rich motif, a central region which exhibits significant homology to the putative C. elegans protein F10E9.6 (Stein et al EMBO J, 13, 1331–1340, 1994) and which also encompasses a PH domain, and a C-terminal SH2 domain. An alignment of the amino acid sequences of GDU, Grb7, Grb10 and F10E9.6 is shown in FIG. 3.

GDU is similar in size to Grb7, Grb10 possessing a more extended N-terminus. The N-terminal region exhibits low sequence homology between GDU, Grb7 and Grb10 apart from a highly conserved amino acid motif PS/AIPNPFPEL. Also of note is the presence of two clusters of basic residues which flank this motif. Overall the N-terminal region of GDU displays a lower proline content than that of Grb7 and Grb10 (GDU amino acids 1–110; 11% proline, Grb10 amino acids 1–113; 15%, Grb7 amino acids 1–103; 23%).

GDU, Grb7 and Grb10 share a central, conserved region of approximately 320 amino acids which exhibits significant homology to a domain found in the C. elegans protein F10E9.6. Over this region, GDU bears 48, 55 and 28% amino acid identify respectively with Grb7, Grb10 and F10E9.6 (FIG. 3). The core of this region is provided by a PH domain (FIGS. 1, 2 and 3), over which GDU exhibits 56, 61 and 35% amino acid identity, respectively, with Grb7, Grb10 and F10E9.6. However, as noted by Ooi et al, (Oncogene 10, 1621–1630, 1995) another region of particularly marked homology spanning approximately 100 amino acids exists amino-terminal to the PH domain (FIG. 3).

The most highly conserved region amongst Grb7 family members is the SH2 domain (FIG. 3). The GDU SH2 domain displays 67 and 74% amino acid identity, respectively, with the corresponding domain in Grb7 and Grb10.

Northern Blot Analysis of GDU Gene Expression

The tissue specificity of GDU gene expression was investigated by hybridizing Northern blots of poly A+ RNA isolated from a variety of human tissues to a GDU specific cDNA probe. GDU gene expression was highest in the testis, ovary, heart, liver, skeletal muscle, kidney and pancreas. Moderate expression was detected in the small intestine, colon, peripheral blood leukocytes, brain and placenta, whilst expression in the spleen, thymus, prostate and lung was low or undetectable. Several mRNA transcripts were detected which displayed tissue-specific variation in their relative abundance. The three most prominent transcripts were approximately 2.3, 2.4 and 2.5 kb. Often co-expressed with one or two of these transcripts was a transcript of approximately 9.5 kb. In the ovary a still larger transcript of undetermined size was also expressed.

Since the Grb14 cDNA was originally isolated from a cDNA library prepared from normal human breast epithelial cells, we were interested in determining the expression profile of Grb14 mRNA in a panel of human breast cancer cell lines. Upon Northern blot analysis of total RNA isolated from 3 normal human breast epithelial cell strains and 19 human breast cancer cell lines, Grb14 gene expression could be detected in HMEC 184 and HMEC-219-4 cells, 6/7 ER+human breast cancer cell lines and 2/12 ER-cell lines (Table 1). Thus Grb14 gene expression appears largely restricted to normal breast epithelial and ER+breast cancer cells. Differential expression of Grb14 was also observed amongst human prostate cancer cell lines. Although Grb14 MRNA expression was undetectable in the normal prostate, low expression could be detected in the PC3 and LnGaP prostate cancer cell lines and high expression in the DU145 line (Table 1).

| Origin | Cell Line | Expression |
|---|---|---|
| Normal human breast epithelial | HMEC 184 | +++ |
|  | HMEC-219-4 | + |
|  | HMEC-1001-7 | – |
| Human breast cancer, ER + | T-47D | +++ |
|  | ZR-75-1 | ++ |
|  | MCF-7 | + |
|  | BT-483 | + |
|  | MDA-MB-134 | + |
|  | MDA-MB-361 | + |
|  | BT-474 | – |
| Human breast cancer, ER– | MDA-MB-330 | + |
|  | MDA-MB-468 | + |
|  | BT-20 | – |
|  | SK-BR-3 | – |
|  | BT-549 | – |
|  | H3578T | – |
|  | DU-4475 | – |
|  | MDA-MB-157 | – |
|  | MDA-MB-175 | – |
|  | MDA-MB-231 | – |
|  | MDA-MB-436 | – |
|  | MDA-MB-453 | – |
| Human prostate cancer | PC3 | + |
|  | LnCaP | + |
|  | DU-145 | ++++ |
| Human epidermoid carcinoma | A431 | – |
| Human embryonic kidney | HEK 293 | ++++ |

Table 1. Expression of Grb14 mRNA in different human cell lines. Total cellular RNA was extracted from the indicated cell lines and subjected to Northern blot analysis using a Grb14 cDNA probe. The relative expression levels of Grb14 mRNA were then scored on a scale from +(low) to ++++ (high). –; undetectable expression.

Expression of Grb14 Protein

In order to characterize the Grb14 protein a polyclonal antiserum was raised against a GST-Grb14 SH2 domain fusion protein. Following affinity purification, this antiserum was used to Western blot cell lysates derived from cell lines in which Grb14 mRNA was either expressed at high levels (DU145 and HEK 293) or was undetectable (A431 and SK-BR-3) (Table 1). The antiserum recognized a protein of approximately 58 kDa in DU145 cells, whilst in HEK 293 cells a tight doublet of this mobility was detected. These bands were not observed upon Western blotting with pre-immune serum or in the cell lines which do not express Grb14 mRNA. This estimated size of Grb14 upon SDS-PAGE is in accordance with the predicted size of the translation product of the Grb14 cDNA (60 kDa).

Since DU145 cells overexpress Grb14 mRNA relative to the two other prostate carcinoma cell lines examined (Table 1), we investigated whether this was accompanied by an upregulation of Grb14 protein expression. Upon Western blot analysis, Grb14 was clearly detectable in DU145, but not PC3 or LnCaP, cell lysates, indicating that Grb14 protein is overexpressed in this cell line.

Phosphorylation of Grb14

In order to characterize further the role of Grb14 in receptor tyrosine kinase signalling, the phosphorylation state of Grb14 was investigated before and after growth factor stimulation. Since the anti-Grb14 antiserum 264 did not immunoprecipitate Grb14 under either native or denaturing conditions, we utilized an expression construct (pRcCMV$_{Flag}$) which tagged Grb14 with the 8 amino acid Flag epitope at the C-terminus. This construct was stably transfected into HEK 293 cells, leading to the isolation of stable clones of cells expressing an epitope-tagged Grb14 which could be immunoprecipitated with the M2 anti-Flag monoclonal antibody and Western blotted with either this antibody or anti-Grb14 antiserum 264. Immunoprecipitation of Grb14 from serum starved cells which were metabolically labelled with $^{32}$P-orthophosphate demonstrated that Grb14 was phosphorylated in this basal state. Phosphoamino acid analysis of the isolated protein demonstrated that phosphorylation was on serine residues.

Treatment of the cells with EGF did not significantly increase this level of phosphorylation, although activation of native EGFRs could be demonstrated by anti-phosphotyrosine blotting of the cell lysates. However, stimulation with PGDF BB resulted in an approximately 1.5 fold increase within 5 min of administration, and transient transfection of a cDNA encoding β-PDGFRs into the cells further amplified this response to approximately 2-fold. The small increase in phosphorylation which occurred when this construct was present in the absence of PGDF BB was presumably due to the constitutive activation of RTKs often observed with this system. Phosphoamino acid analysis demonstrated that the PDGF-induced increases in Grb14 phosphorylation also occurred on serine residues.

As will be recognised by persons skilled in this field the present inventors have identified a novel signalling molecule which they pave designated GDU or Grb14. GDU has the potential to be used as a prognostic indicator/tumour marker in both breast and prostate cancer. In addition, as GDU may influence invasive/ metastatic behaviour it may also serve as a marker of invasive/metastatic disease in these and other cancers. Finally, the involvement of GDU in signalling by the PDGFR suggests that it may represent a therapeutic target in diseases or conditions in which PDGF plays a regulatory role.

Signalling via GDU could be targeted by competitive peptides or dominant negative mutants, or restored by gene therapy. The information provided herein will clearly assist in the rational design of a GDU antagonist.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

SEQUENCE LISTING

<160> NUMBER OF SEQ ID NOS: 5

<210> SEQ ID NO 1
<211> LENGTH: 2404
<212> TYPE: DNA
<213> ORGANISM: Homo sapiens

<400> SEQUENCE: 1

```
cggatgaggg tcagggctgc gcggacccct atcccgcctg cgtcctcccg gcaagcccag     60
cgggagcgcc cgctcggctg ggtccccgcc tccagcgcgc cggggccgcc cagaccctgg    120
gctcagcctc gcgccccggt gcccacctga ggaggcggcg gtcccggcct cgcgtcccgg    180
atgggacggc gcgggagcaa tgccagtggc cccgagcgcc ccgggccacg cgcggggccg    240
gccagccgct ctcgcgccct ccccgccccc tccgcgcctt gcctcgccgc ccgcgcgccc    300
cacccaccgg ccgctcctcc cctctcccca ccctcctcct ccgcccccctc ccctcccccg   360
ccgcctcgca gatagctcgg ccgcgcgtct cagccgccgg ggccccgagc gcaggcggcg    420
aggccaccac acctgcagag cgctcgggct gcctaggcgg cacctcgcct cccgccgcgc    480
aaacccttc tccccacgcg ccgagtctcc catgacgccc gagcccccg gccggcgaca      540
atgaccactt ccctgcaaga tgggcagagc gccgcgagca gggcggctgc ccgggattcg    600
ccgctggccg cccaggtgtg tggcgctgcc caggggaggg gcgacgccca cgacctggcg    660
ccggcccccct ggctgcacgc gcgagcgctc ctgccccttc cggacgggac ccgcggctgt   720
gctgcagaca ggagaaaaaa gaaagatctt gatgttccgg aaatgccatc tattccaaac    780
ccttttcctg agctatgctg ttctccaatt acatctgtgt tgtcagcaga cctatttccc    840
aaagcaaatt caaggaaaaa acaggtgatt aaagtataca gtgaagatga aaccagcagg    900
gctttagatg tacccagtga cataacggct cgagatgttt gtcagctgtt gatcctgaag    960
aatcattaca ttgatgacca cagctggacc cttttttgagc acctgcctca cataggtgta   1020
gaaagaacaa tagaagacca cgaactggtg attgaagtgc tatccaactg ggggatagaa   1080
gaagaaaaca aactatactt tagaaaaaat tatgccaaat atgagttctt taaaaaccca   1140
atgtattttt ttccagagca tatggtatct tttgcaactg aaaccaatgg tgaaatatcc   1200
cccacacaga ttttgcagat gtttctgagt tcaagcacat atcctgaaat tcatggtttc   1260
ttacatgcga aagaacaggg aaagaagtct tggaaaaaaa tttacttttt tctaagaaga   1320
tctggtttat attttctac taaggaaca tcaaggaac cgcggcattt gcagtttttc      1380
agcgaatttg gcaatagtga tatttatgtg tcactggcag gcaaaaaaaa acatggagca   1440
ccgactaact atggattctg ctttaagcct aacaaagcgg gagggccccg agacctgaaa   1500
atgctctgtg cagaagaaga gcagagtagg acgtgctggg tgaccgcgat tagattgctt   1560
aagtatggca tgcagctgta ccagaattat atgcatccat atcaaggtag aagtggctgc   1620
agttcacaga gcatatcacc tatgagaagt atatcagaga attccctggt agcaatggac   1680
ttctcaggcc agaaaagcag agttatagaa aatcccactg aagcccttc agttgcggtt    1740
gaagaaggac tcgcttggag gaaaaaagga tgtttacgcc tgggcactca cggtagcccc   1800
actgcctctt cacagagctc tgccacaaac atggctatcc accggtccca gccatggttt   1860
caccacaaaa tttctagaga tgaggctcag cgattgatta ttcagcaagg acttgtggat   1920
ggagttttct tggtacggga tagtcagagt aaccccaaaa ctttcgtact gtcaatgagt   1980
```

-continued

```
catggacaaa aaataaagca ctttcaaatt ataccagtag aagatgacgg tgaaatgttc     2040
cacacactgg atgatggcca cacaagattt acagatctaa tacagctggt ggagttctat     2100
caactcaata agggcgttct tccttgcaag ttgaaacatt attgtgctag gattgctctc     2160
tagacaagcc agaagtgact tattaaacta ttgaaggaaa aggactcaag aaaaataata     2220
aaagaccata aataagggcg aaaacattat catgtgaaaa gaatgtattt cacctgcaag     2280
ttacaaaaaa atagtttgtg cattgcaaat aagcaaagac ttggattgac tttacattca     2340
tcatttaaaa ttcattagtt aaaattaaac cttaggaaaa aaaaaaaaa aaaaaaaaa     2400 aaaa                                                                 2404
```

<210> SEQ ID NO 2
<211> LENGTH: 540
<212> TYPE: PRT
<213> ORGANISM: Homo sapiens

<400> SEQUENCE: 2

```
Met Thr Thr Ser Leu Gln Asp Gly Gln Ser Ala Ala Ser Arg Ala Ala
 1               5                  10                  15

Ala Arg Asp Ser Pro Leu Ala Ala Gln Val Cys Gly Ala Ala Gln Gly
            20                  25                  30

Arg Gly Asp Ala His Asp Leu Ala Pro Ala Pro Trp Leu His Ala Arg
        35                  40                  45

Ala Leu Leu Pro Leu Pro Asp Gly Thr Arg Gly Cys Ala Ala Asp Arg
    50                  55                  60

Arg Lys Lys Lys Asp Leu Asp Val Pro Glu Met Pro Ser Ile Pro Asn
65                  70                  75                  80

Pro Phe Pro Glu Leu Cys Cys Ser Pro Ile Thr Ser Val Leu Ser Ala
                85                  90                  95

Asp Leu Phe Pro Lys Ala Asn Ser Arg Lys Lys Gln Val Ile Lys Val
            100                 105                 110

Tyr Ser Glu Asp Glu Thr Ser Arg Ala Leu Asp Val Pro Ser Asp Ile
        115                 120                 125

Thr Ala Arg Asp Val Cys Gln Leu Leu Ile Leu Lys Asn His Tyr Ile
    130                 135                 140

Asp Asp His Ser Trp Thr Leu Phe Glu His Leu Pro His Ile Gly Val
145                 150                 155                 160

Glu Arg Thr Ile Glu Asp His Glu Leu Val Ile Glu Val Leu Ser Asn
                165                 170                 175

Trp Gly Ile Glu Glu Glu Asn Lys Leu Tyr Phe Arg Lys Asn Tyr Ala
            180                 185                 190

Lys Tyr Glu Phe Phe Lys Asn Pro Met Tyr Phe Phe Pro Glu His Met
        195                 200                 205

Val Ser Phe Ala Thr Glu Thr Asn Gly Glu Ile Ser Pro Thr Gln Ile
    210                 215                 220

Leu Gln Met Phe Leu Ser Ser Thr Tyr Pro Glu Ile His Gly Phe
225                 230                 235                 240

Leu His Ala Lys Glu Gln Gly Lys Lys Ser Trp Lys Lys Ile Tyr Phe
                245                 250                 255

Phe Leu Arg Arg Ser Gly Leu Tyr Phe Ser Thr Lys Gly Thr Ser Lys
            260                 265                 270

Glu Pro Arg His Leu Gln Phe Phe Ser Glu Phe Gly Asn Ser Asp Ile
        275                 280                 285
```

-continued

```
Tyr Val Ser Leu Ala Gly Lys Lys His Gly Ala Pro Thr Asn Tyr
    290                 295                 300
Gly Phe Cys Phe Lys Pro Asn Lys Ala Gly Pro Arg Asp Leu Lys
305                 310                 315                 320
Met Leu Cys Ala Glu Glu Gln Ser Arg Thr Cys Trp Val Thr Ala
                325                 330                 335
Ile Arg Leu Leu Lys Tyr Gly Met Gln Leu Tyr Gln Asn Tyr Met His
                340                 345                 350
Pro Tyr Gln Gly Arg Ser Gly Cys Ser Ser Gln Ser Ile Ser Pro Met
                355                 360                 365
Arg Ser Ile Ser Glu Asn Ser Leu Val Ala Met Asp Phe Ser Gly Gln
    370                 375                 380
Lys Ser Arg Val Ile Glu Asn Pro Thr Glu Ala Leu Ser Val Ala Val
385                 390                 395                 400
Glu Glu Gly Leu Ala Trp Arg Lys Lys Gly Cys Leu Arg Leu Gly Thr
                405                 410                 415
His Gly Ser Pro Thr Ala Ser Ser Gln Ser Ser Ala Thr Asn Met Ala
                420                 425                 430
Ile His Arg Ser Gln Pro Trp Phe His His Lys Ile Ser Arg Asp Glu
                435                 440                 445
Ala Gln Arg Leu Ile Ile Gln Gln Gly Leu Val Asp Gly Val Phe Leu
    450                 455                 460
Val Arg Asp Ser Gln Ser Asn Pro Lys Thr Phe Val Leu Ser Met Ser
465                 470                 475                 480
His Gly Gln Lys Ile Lys His Phe Gln Ile Ile Pro Val Glu Asp Asp
                485                 490                 495
Gly Glu Met Phe His Thr Leu Asp Asp Gly His Thr Arg Phe Thr Asp
                500                 505                 510
Leu Ile Gln Leu Val Glu Phe Tyr Gln Leu Asn Lys Gly Val Leu Pro
    515                 520                 525
Cys Lys Leu Lys His Tyr Cys Ala Arg Ile Ala Leu
    530                 535                 540

<210> SEQ ID NO 3
<211> LENGTH: 535
<212> TYPE: PRT
<213> ORGANISM: Mus musculus

<400> SEQUENCE: 3

Met Glu Leu Asp Leu Ser Pro Thr His Leu Ser Ser Pro Glu Asp
  1               5                  10                  15
Val Cys Pro Thr Pro Ala Thr Pro Pro Glu Thr Pro Pro Pro Asp
                 20                  25                  30
Asn Pro Pro Gly Asp Val Lys Arg Ser Gln Pro Leu Pro Ile Pro
                 35                  40                  45
Ser Ser Arg Lys Leu Arg Glu Glu Phe Gln Ala Thr Ser Leu Pro
 50                  55                  60
Ser Ile Pro Asn Pro Phe Pro Glu Leu Cys Ser Pro Ser Gln Lys
 65                  70                  75                  80
Pro Ile Leu Gly Gly Ser Ser Gly Ala Arg Gly Leu Leu Pro Arg Asp
                 85                  90                  95
Ser Ser Arg Leu Cys Val Val Lys Val Tyr Ser Glu Asp Gly Ala Cys
                100                 105                 110
Arg Ser Val Glu Val Ala Ala Gly Ala Thr Ala Arg His Val Cys Glu
    115                 120                 125
```

```
Met Leu Val Gln Arg Ala His Ala Leu Ser Asp Glu Ser Trp Gly Leu
    130                 135                 140

Val Glu Ser His Pro Tyr Leu Ala Leu Glu Arg Gly Leu Glu Asp His
145                 150                 155                 160

Glu Phe Val Val Glu Val Gln Glu Ala Trp Pro Val Gly Gly Asp Ser
                165                 170                 175

Arg Phe Ile Phe Arg Lys Asn Phe Ala Lys Tyr Glu Leu Phe Lys Ser
            180                 185                 190

Pro Pro His Thr Leu Phe Pro Glu Lys Met Val Ser Ser Cys Leu Asp
        195                 200                 205

Ala Gln Thr Gly Ile Ser His Glu Asp Leu Ile Gln Asn Phe Leu Asn
    210                 215                 220

Ala Gly Ser Phe Pro Glu Ile Gln Gly Phe Leu Gln Leu Arg Gly Ser
225                 230                 235                 240

Gly Arg Gly Ser Gly Arg Lys Leu Trp Lys Arg Phe Cys Phe Leu
                245                 250                 255

Arg Arg Ser Gly Leu Tyr Tyr Ser Thr Lys Gly Thr Ser Lys Asp Pro
            260                 265                 270

Arg His Leu Gln Tyr Val Ala Asp Val Asn Glu Ser Asn Val Tyr Val
        275                 280                 285

Val Thr Gln Gly Arg Lys Leu Tyr Gly Met Pro Thr Asp Phe Gly Phe
    290                 295                 300

Cys Val Lys Pro Asn Lys Leu Arg Asn Gly His Lys Gly Leu His Ile
305                 310                 315                 320

Phe Cys Ser Glu Asp Glu Gln Ser Arg Thr Cys Trp Leu Ala Ala Phe
                325                 330                 335

Arg Leu Phe Lys Tyr Gly Val Gln Leu Tyr Lys Asn Tyr Gln Gln Ala
            340                 345                 350

Gln Ser Arg His Leu Arg Leu Ser Tyr Leu Gly Ser Pro Pro Leu Arg
        355                 360                 365

Ser Val Ser Asp Asn Thr Leu Val Ala Met Asp Phe Ser Gly His Ala
    370                 375                 380

Gly Arg Val Ile Asp Asn Pro Arg Glu Ala Leu Ser Ala Ala Met Glu
385                 390                 395                 400

Glu Ala Gln Ala Trp Arg Lys Lys Thr Asn His Arg Leu Ser Leu Pro
                405                 410                 415

Thr Thr Cys Ser Gly Ser Ser Leu Ser Ala Ala Ile His Arg Thr Gln
            420                 425                 430

Pro Trp Phe His Gly Arg Ile Ser Arg Glu Glu Ser Gln Arg Leu Ile
        435                 440                 445

Gly Gln Gln Gly Leu Val Asp Gly Val Phe Leu Val Arg Glu Ser Gln
    450                 455                 460

Arg Asn Pro Gln Gly Phe Val Leu Ser Leu Cys His Leu Gln Lys Val
465                 470                 475                 480

Lys His Tyr Leu Ile Leu Pro Ser Glu Asp Glu Gly Cys Leu Tyr Phe
                485                 490                 495

Ser Met Asp Glu Gly Gln Thr Arg Phe Thr Asp Leu Leu Gln Leu Val
            500                 505                 510

Glu Phe His Gln Leu Asn Arg Gly Ile Leu Pro Cys Leu Leu Arg His
        515                 520                 525

Cys Cys Ala Arg Val Ala Leu
530                 535
```

```
<210> SEQ ID NO 4
<211> LENGTH: 621
<212> TYPE: PRT
<213> ORGANISM: Mus musculus

<400> SEQUENCE: 4

Met Asn Asp Ile Asn Ser Val Glu Ser Leu Asn Ser Ala Cys
 1               5                  10                  15

Asn Met Gln Ser Asp Thr Asp Thr Ala Pro Leu Leu Glu Asp Gly Gln
            20                  25                  30

His Ala Ser Asn Gln Gly Ala Ala Ser Ser Arg Gly Gln Pro Gln
            35                  40                  45

Ala Ser Pro Arg Gln Lys Met Gln Arg Ser Gln Pro Val His Ile Leu
    50                  55                  60

Arg Arg Leu Gln Glu Glu Asp Gln Gln Leu Arg Thr Ala Ser Leu Pro
65                  70                  75                  80

Ala Ile Pro Asn Pro Phe Pro Glu Leu Thr Gly Ala Ala Pro Gly Ser
                85                  90                  95

Pro Pro Ser Val Ala Pro Ser Ser Leu Pro Pro Pro Ser Gln Pro
            100                 105                 110

Pro Ala Lys His Cys Gly Arg Cys Glu Lys Trp Ile Pro Gly Glu Asn
            115                 120                 125

Thr Arg Gly Asn Gly Lys Arg Lys Ile Trp Arg Trp Gln Phe Pro Pro
    130                 135                 140

Gly Phe Gln Leu Ser Lys Leu Thr Arg Pro Gly Leu Trp Thr Lys Thr
145                 150                 155                 160

Thr Ala Arg Phe Ser Lys Lys Gln Pro Lys Asn Gln Cys Pro Thr Asp
                165                 170                 175

Thr Val Asn Pro Val Ala Arg Met Pro Thr Ser Gln Met Glu Lys Leu
            180                 185                 190

Arg Leu Arg Lys Asp Val Lys Val Phe Ser Glu Asp Gly Thr Ser Lys
            195                 200                 205

Val Val Glu Ile Leu Thr Asp Met Thr Ala Arg Asp Leu Cys Gln Leu
    210                 215                 220

Leu Val Tyr Lys Ser His Cys Val Asp Asp Asn Ser Trp Thr Leu Val
225                 230                 235                 240

Glu His His Pro Gln Leu Gly Leu Glu Arg Cys Leu Glu Asp His Glu
                245                 250                 255

Ile Val Val Gln Val Glu Ser Thr Met Pro Ser Glu Ser Lys Phe Leu
            260                 265                 270

Phe Arg Lys Asn Tyr Ala Lys Tyr Glu Phe Phe Lys Asn Pro Val Asn
        275                 280                 285

Phe Phe Pro Asp Gln Met Val Asn Trp Cys Gln Gln Ser Asn Gly Gly
    290                 295                 300

Gln Ala Gln Leu Leu Gln Asn Phe Leu Asn Thr Ser Ser Cys Pro Glu
305                 310                 315                 320

Ile Gln Gly Phe Leu Gln Val Lys Glu Val Gly Arg Lys Ser Trp Lys
                325                 330                 335

Lys Leu Tyr Val Cys Leu Arg Arg Ser Gly Leu Tyr Tyr Ser Thr Lys
            340                 345                 350

Gly Thr Ser Lys Glu Pro Arg His Leu Gln Leu Leu Ala Asp Leu Glu
        355                 360                 365

Glu Ser Ser Ile Phe Tyr Leu Ile Ala Gly Lys Lys Gln Tyr Asn Ala
    370                 375                 380
```

-continued

```
Pro Asn Glu His Gly Met Cys Ile Lys Pro Asn Lys Ala Lys Thr Glu
385                 390                 395                 400

Met Lys Glu Leu Arg Leu Leu Cys Ala Glu Asp Glu Gln Ile Arg Thr
            405                 410                 415

Cys Trp Met Thr Ala Phe Arg Leu Leu Lys Tyr Gly Met Leu Leu Tyr
                420                 425                 430

Gln Asn Tyr Arg Ile Pro Gln Arg Lys Gly Leu Pro Pro Pro Phe Asn
            435                 440                 445

Ala Pro Met Arg Ser Val Ser Glu Asn Ser Leu Ala Met Asp Phe
450                 455                 460

Ser Gly Gln Ile Gly Arg Val Ile Asp Asn Pro Ala Glu Ala Gln Ser
465                 470                 475                 480

Ala Ala Leu Glu Glu Gly His Ala Trp Arg Asn Gly Ser Thr Arg Met
                485                 490                 495

Asn Ile Leu Ser Ser Gln Ser Pro Leu His Pro Ser Thr Leu Asn Ala
                500                 505                 510

Val Ile His Arg Thr Gln His Trp Phe His Gly Arg Ile Ser Arg Glu
            515                 520                 525

Glu Ser His Arg Ile Ile Lys Gln Gln Gly Leu Val Asp Gly Leu Phe
530                 535                 540

Leu Leu Arg Asp Ser Gln Ser Asn Pro Lys Ala Phe Val Leu Thr Leu
545                 550                 555                 560

Cys His His Gln Lys Ile Lys Asn Phe Gln Ile Leu Pro Cys Glu Asp
                565                 570                 575

Asp Gly Gln Thr Phe Phe Thr Leu Asp Asp Gly Asn Thr Lys Phe Ser
            580                 585                 590

Asp Leu Ile Gln Leu Val Asp Phe Tyr Gln Leu Asn Lys Gly Val Leu
            595                 600                 605

Pro Cys Lys Leu Lys His His Cys Ile Arg Val Ala Leu
        610                 615                 620

<210> SEQ ID NO 5
<211> LENGTH: 339
<212> TYPE: PRT
<213> ORGANISM: Caenorhabditis elegans

<400> SEQUENCE: 5

Val Lys Phe Phe Val Glu Asp Gly Glu Ala Leu Gln Leu Leu Ile Asp
1               5                   10                  15

Glu Arg Trp Thr Val Ala Asp Thr Leu Lys Gln Leu Ala Glu Lys Asn
                20                  25                  30

His Ile Ala Leu Met Glu Asp His Cys Ile Val Glu Glu Tyr Pro Glu
            35                  40                  45

Leu Tyr Ile Lys Arg Val Tyr Glu Asp His Glu Lys Val Val Glu Asn
        50                  55                  60

Ile Gln Met Trp Val Gln Asp Ser Pro Asn Lys Leu Tyr Phe Met Arg
65                  70                  75                  80

Arg Pro Asp Lys Tyr Ala Phe Ile Ser Arg Pro Glu Leu Tyr Leu Leu
                85                  90                  95

Thr Pro Lys Thr Ser Asp His Met Glu Ile Pro Ser Gly Asp Gln Trp
            100                 105                 110

Thr Ile Asp Val Lys Gln Lys Phe Val Ser Glu Tyr Phe His Arg Glu
        115                 120                 125

Pro Val Val Pro Pro Glu Met Glu Gly Phe Leu Tyr Leu Lys Ser Asp
```

-continued

```
            130                 135                 140
Gly Arg Lys Ser Trp Lys Lys His Tyr Phe Val Leu Arg Pro Ser Gly
145                 150                 155                 160

Leu Tyr Tyr Ala Pro Lys Ser Lys Pro Thr Thr Lys Asp Leu Thr
                165                 170                 175

Cys Leu Met Asn Leu His Ser Asn Gln Val Tyr Thr Gly Ile Gly Trp
                180                 185                 190

Glu Lys Lys Tyr Lys Ser Pro Thr Pro Trp Cys Ile Ser Ile Lys Leu
        195                 200                 205

Thr Ala Leu Gln Met Lys Arg Ser Gln Phe Ile Lys Tyr Ile Cys Ala
        210                 215                 220

Glu Asp Glu Met Thr Phe Lys Lys Trp Leu Val Ala Leu Arg Ile Ala
225                 230                 235                 240

Lys Asn Gly Ala Glu Leu Leu Glu Asn Tyr Glu Arg Ala Cys Gln Ile
                245                 250                 255

Arg Arg Glu Thr Leu Gly Pro Ala Ser Ser Met Ser Ala Ala Ser Ser
                260                 265                 270

Ser Thr Ala Ile Ser Glu Val Pro His Ser Leu Ser His His Gln Arg
        275                 280                 285

Thr Pro Ser Val Ala Ser Ser Ile Gln Leu Ser Ser His Met Met Asn
        290                 295                 300

Asn Pro Thr His Pro Leu Ser Val Asn Val Arg Asn Gln Ser Pro Ala
305                 310                 315                 320

Ser Phe Ser Val Asn Ser Cys Gln Gln Ser His Pro Ser Arg Thr Ser
                325                 330                 335

Ala Lys Leu
```

1. A monoclonal antibody which binds to a GDU polypeptide, the polypeptide having an amino acid sequence as shown in SEQ ID NO:2.

2. A method of detecting the presence of GDU in a sample, the method comprising reacting the sample with a monoclonal antibody as claimed in claim 1 and detecting the binding of the antibody.

* * * * *